United States Patent [19]

Stead

[11] Patent Number: 4,574,957

[45] Date of Patent: Mar. 11, 1986

[54] PACKING OF SURGICAL NEEDLE

[75] Inventor: Michael J. Stead, Verwoerdburg, South Africa

[73] Assignee: Ethicon, Inc., Somerville, N.J.

[21] Appl. No.: 695,149

[22] Filed: Jan. 25, 1985

[30] Foreign Application Priority Data

Mar. 30, 1984 [ZA] South Africa .................. 84/2430

[51] Int. Cl.⁴ .......................................... A61L 17/02
[52] U.S. Cl. ................................. 206/63.3; 206/388; 206/491
[58] Field of Search ............... 206/63.3, 388, 491, 206/353, 392

[56] References Cited

U.S. PATENT DOCUMENTS 4,142,628  3/1979  Marocco et al. ............. 206/63.3
4,249,656  2/1981  Cerwin et al. .............. 206/63.3
4,284,194  8/1981  Flatau ....................... 206/63.3
4,406,363  9/1983  Aday ........................ 206/63.3
4,412,614 11/1983  Ivanov et al. ............... 206/63.3
4,491,218  1/1985  Aday ........................ 206/63.3

Primary Examiner—Joseph Man-Fu Moy
Attorney, Agent, or Firm—Robert L. Minier

[57]   ABSTRACT

The invention provides a disposable suture package containing a curved surgical needle to which a suture is attached. A flattened envelope has a slot extending along part of its periphery through which a pull tab, fast with a needle carrier inside the envelope, projects outwardly from the interior of the envelope. The needle carrier is movable in the interior of the envelope towards the slot in response to a pull on the tab and has a needle-engaging formation for urging the needle towards the slot and into engagement with a cam formation fast with the envelope, to urge one end of the needle out of the slot and into a position in which it stands free of the envelope and tab.

4 Claims, 6 Drawing Figures

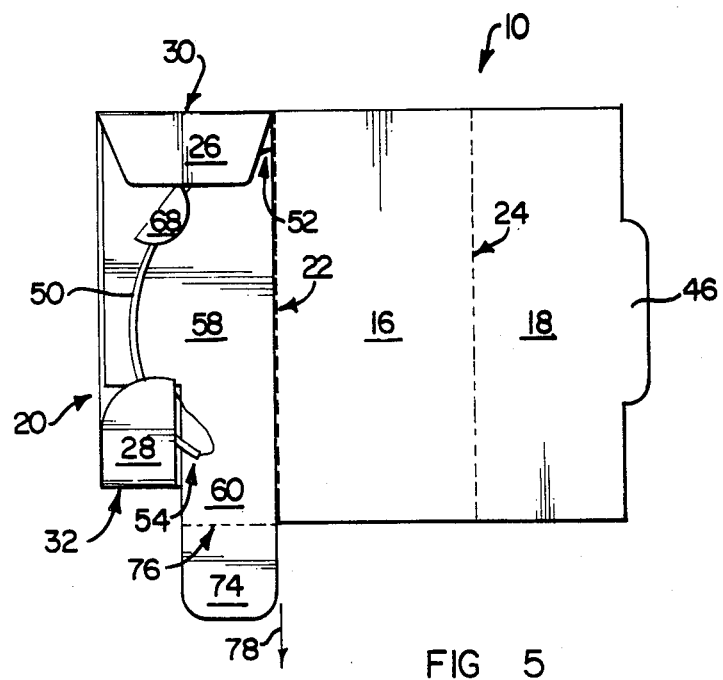
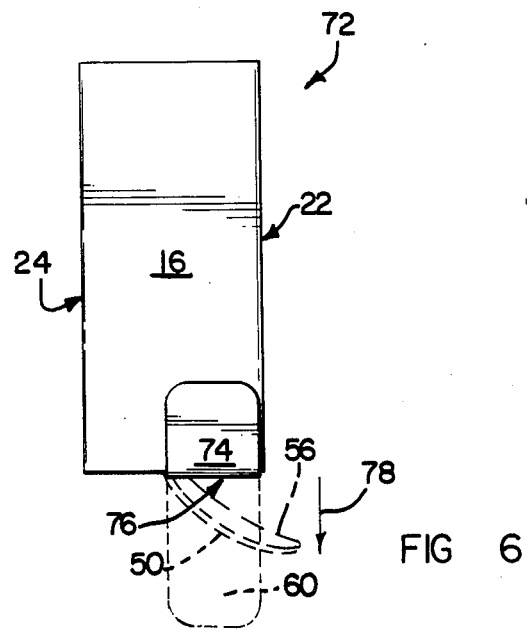

PACKING OF SURGICAL NEEDLE

This invention relates to the packaging of a surgical needle having a suture attached thereto. More particularly, the invention relates to a disposable package suitable for the retailing of a single curved surgical needle having a suture attached thereto.

According to the invention a disposable suture package contains a curved surgical needle having a suture attached thereto and comprises a flattened envelope having a slot extending along part of its periphery through which a pull tab, fast with a needle carrier inside the envelope, projects outwardly from the interior of the envelope, the needle carrier being movable in the interior of the envelope towards the slot in response to a pull on the tab and having a needle-engaging formation fast therewith for urging the needle towards the slot and into engagement with a cam formation fast with the envelope, to urge one end of the needle out of the slot and into a position in which it stands free of the envelope and tab.

The envelope may be elongated and rectangular in outline and is made of folded sheet material such as paper, cardboard, or the like, the envelope having a periphery having a pair of longer or side edges and a pair of shorter or end edges and a slot extending along one of the shorter or end edges of the periphery of the envelope and the needle extending at least roughly longitudinally along the interior of the enveloe with its trailing end, to which the suture is attached, presented towards the slot. The pull tab and needle carrier may be integral with each other, being made of sheet material, e.g. material similar to that of the envelope, the needle-engaging formation of the needle carrier being a flap formed from the sheet material of the needle carrier and being engageable with the convex side of the needle at a position adjacent the end of the needle remote from the slot of the envelope.

In use, the needle will typically lie flat in the envelope, with its opposite ends nearer to one of the longer or side edges of the envelope than the other, the slot extending partially along said shorter edge of the envelope away from said longer edge, so that the trailing end of the needle is adjacent the corner of the envelope between said longer edge and shorter edge at one end of the slot, the remainder of said shorter edge being closed and the material of the envelope closing the opposite end of the slot acting as the cam formation for engaging the needle in use. The outwardly projecting part of the pull tab may be folded over onto the outer surface of the envelope and stuck thereto, to provide the package with an uninterrupted periphery. The needle carrier may be held captive in the interior of the package.

In use, when the tab is pulled outwardly through the slot, the flap of the needle carrier engages the convex side of the needle and tends to urge the needle longitudinally towards the slot and also laterally towards the longer edge of the envelope nearest the ends of the needle, the part of the convex side of the needle which is nearest the slot then engaging the end of the slot remote from said longer edge of the envelope, while the opposite, pointed or leading end of the needle engages the inside of the fold forming said longer edge of the envelope. Said longer edge of the envelope and said end of the slot, upon further pulling of the tab, act as cam formations which respectively engage the pointed end of the needle and the convex side of the needle near its trailing end and cause the needle, as it is moved towards and into the slot by the flap on the needle carrier, to emerge from the slot, trailing end first, and cause the needle to alter its orientation relative to the envelope as it emerges, so that its trailing end projects laterally outwardly of said longer edge of the envelope, into a position in which it stands free of the envelope and pull tab.

Broadly, the invention extends also to a disposable needle package containing a surgical needle and comprising a flattened envelope provided with a needle carrier in its interior on which a needle is supported, the carrier having a pull tab fast therewith and projecting outwardly from a slot in the envelope, the carrier being movable in the interior of the envelope towards the slot in response to a pull on the tab, into a position in which the needle is at least partially exposed and projects form the interior of the package.

The needle may have a suture attached thereto, the needle carrier being held captive in the interior of the envelope. The slot may extend along part of the periphery of the envelope, the needle carrier having a needle-engaging formation fast therewith for urging the needle towards the slot and into engagement with a cam formation fast with the envelope, to urge one end of the needle out of the slot and into a position in which it stands free of the envelope and the tab.

The invention will now be described, by way of example, with reference to the accompanying diagrammatic drawings, in which FIG. 1 shows a plan view outline of a sheet material blank from which an envelope for a package according to the invention is folded;

FIG. 5 shows the blank of FIG. 4 in a yet further folded and closed position; and FIG. 6 shows the blank of FIG. 5 fully folded to form a suture package according to the invention.

Figure 1:
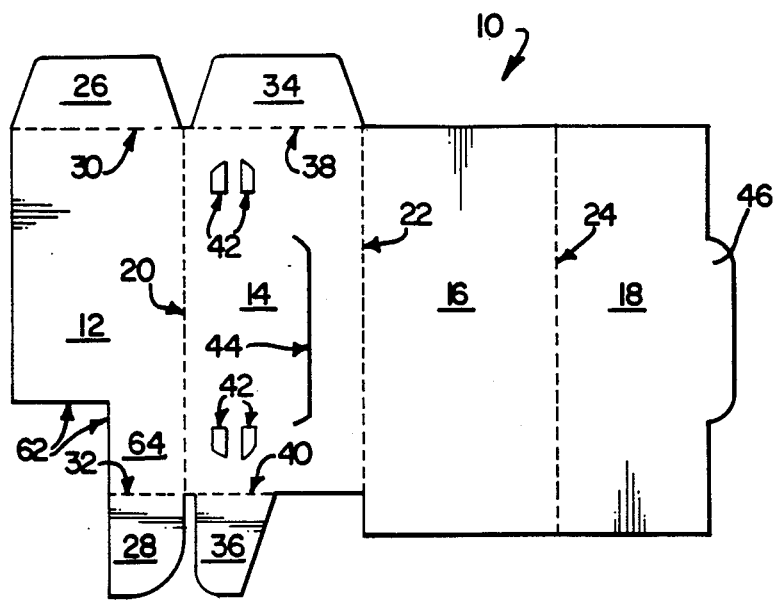

With reference to FIG. 1, reference numeral 10 generally designates a blank, suitably made of thin cardboard or strong paper, from which a package in accordance with the invention is folded. The blank is divided, broadly, into four elongated rectangular panels, respectively designated 12, 14, 16 and 18. A fold line 20, defined by a row of score marks, separates the panel 12 from the panel 14, the panel 14 in turn being separated from the panel 16 by a similar fold line 22, and the panel 16 from the panel 18 by a yet further similar fold line 24. Panel 12 is provided with a pair of flaps 26, 28 at opposite ends thereof, separated therefrom respectively by fold lines 30, 32; and panel 14 also has flaps, designated respectively 34 and 36 at opposite ends thereof, separated therefrom by respective fold lines 38 and 40. Fold lines 30, 32 and 38, 40 are also defined by rows of score marks.

Panel 14 has, adjacent its ends respectively and somewhat closer to the panel 12 than the panel 16, two pairs of windows or openings 42 therethrough, and, longitudinally between the two pairs of openings 42 but somewhat nearer to the panel 16 than the openings 42, a slot 44. The panel 18 in turn has a closure flap 46 receivable in the slot 44, for closing a package folded from the blank 10.

Figure 2:
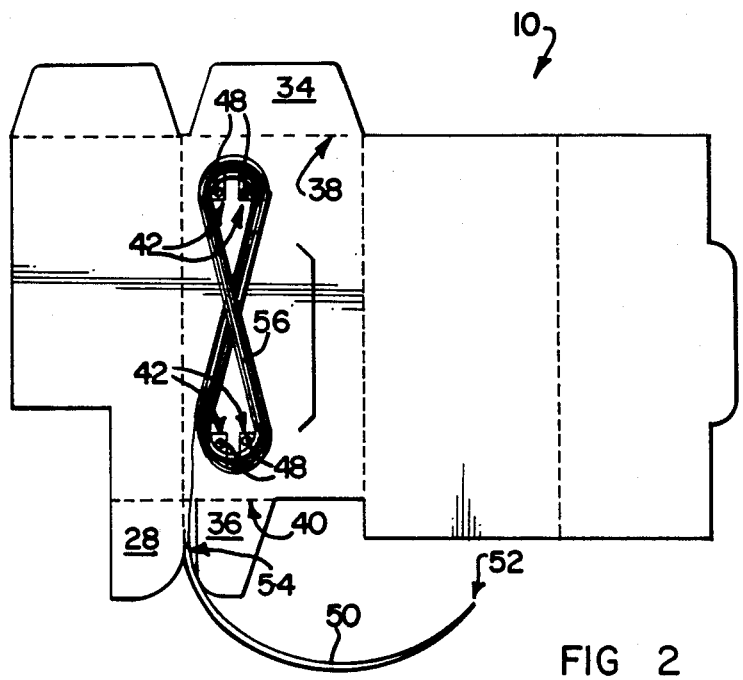
FIG. 2 shows the blank of FIG. 1 in use when a needle and suture are being inserted therein.

With reference now also to FIG. 2, in which the same reference numerals refer to the same parts, unless otherwise specified, the blank 10 of FIG. 1 in use is laid out flat on a work surface. Two pairs of spaced upright pins or pegs (shown at 48 in FIG. 2) project upwardly from the work surface, through the openings 42. An arcuate, part-circular curved needle 50 having a pointed leading end 52 and a trailing end 54 to which a suture 56 is attached, is then placed in position on the blank 10. This is effected by winding the suture in a figure-8 pattern around the pins 48 by hand, as shown in FIG. 2, starting with the end of the suture 56 remote from the needle 50. When most of the suture 56 has been wound around the pins 48 as shown in FIG. 2, a short length remaining unwound and attached to the trailing end 52 of the needle 50, the flaps 34 and 36 are folded over and inwardly respectively about the fold lines 38, 40, on top of the suture 56. This is shown in FIG. 3, in which, again, the same reference numerals are used for the same parts, unless otherwise specified.

Figure 3:
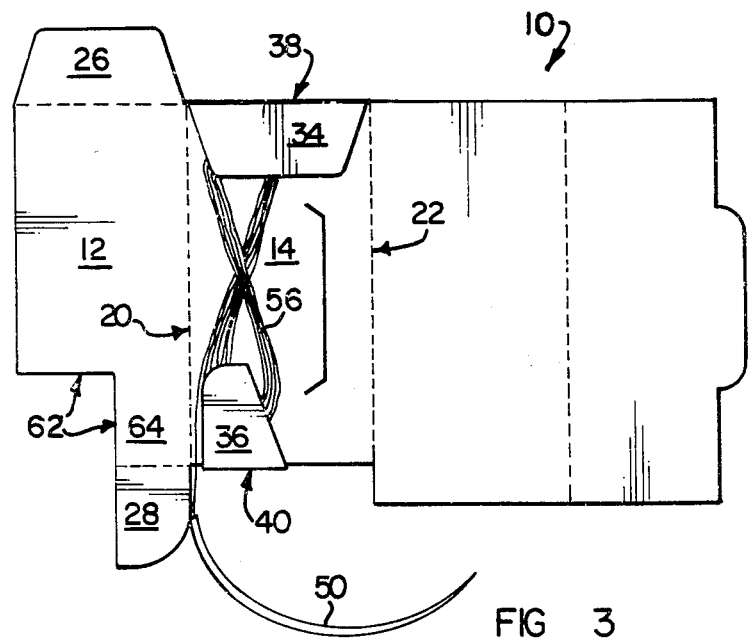
FIG. 3 shows the blank of FIG. 2 in a partially folded and closed position.

During this folding the needle 50 and the unwound portion of the suture 56 attached thereto, are at one end of the panel 14, adjacent the flaps 36 and 28, as shown in FIGS. 2 and 3. At substantially the same time as the flaps 34 and 36 are folded over onto the suture 56, the blank 10 is raised as a whole from the pins 48 and is placed on an upwardly facing work surface for further folding and assembly.

Figure 4:
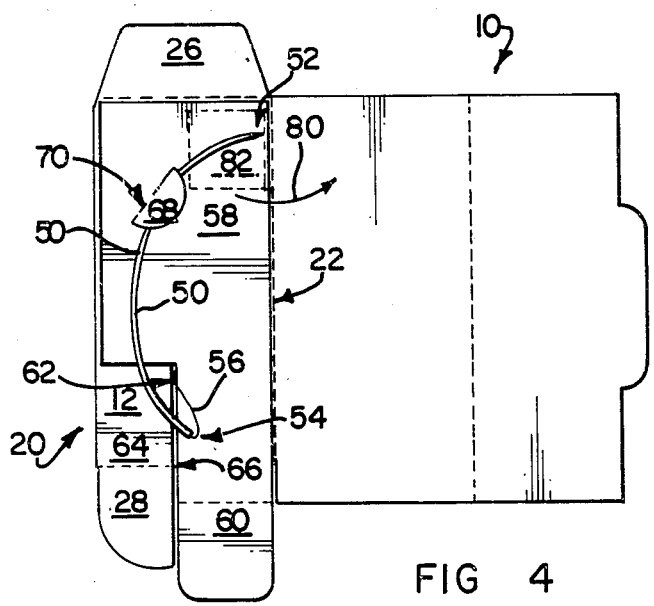
FIG. 4 shows the blank of FIG. 3, in a further folded and closed position, after a pull tab and needle carrier for a package according to the invention have been inserted into position and the needle located on the needle carrier.

The panel 12 is then folded, about the fold line 20, inwardly over and onto the panel 14 to hold down the flaps 34 and 36, which in turn hold the wound suture against the panel 14 in its figure-8 pattern. A needle carrier 58 of similar paper or cardboard and having an integral pull tab 60 fast therewith is then placed in position on top of the folded-over panel 12, as shown in FIG. 4, in which, again, like reference numerals are used to designate like parts. The needle 50 is then placed on the carrier 58, which is in the form of a rectangular panel, as shown in FIG. 4.

In this regard it will be noted that the panel 12 has a cut-out corner portion removed therefrom as shown at 62, to leave a strip 64 of material forming part of the panel 12, to which the flap 28 is connected. The width of this strip 64 and the width of the tab 60 are such that, as shown in FIG. 4, a slot 66 is defined between their adjacent edges, which is closed at one end and which is open at its other end. During insertion of the needle 50 into position on the carrier 58, the needle and the unwound portion of suture 56 attached thereto are moved into position through this slot 66 via its open end, so that the suture, as shown in FIG. 4, extends from the needle through the slot 66, and between the tab 60 and strip 64, to where the remainder of the suture is wound in its figure-8 pattern on the panel 14 and under the panel 12 and flaps 34, 36. With reference to FIG. 4 it will be noted that the needle 50 has its pointed or leading end 52 adjacent the fold line 22, from which the needle curves towards the fold line 20, and then back towards the fold line 22, from which its trailing end 54 is spaced. The leading end 52 is adjacent the flap 26 and the trailing end 54 is adjacent the flap 28. The needle 50 is held in this position by a needle-engaging formation in the form of a flap 68 formed in the panel of the carrier 58. The flap 68 is semi-circular in outline, and is connected to the remainder of the panel of the carrier 58 by a fold line 70, the flap 68 engaging the convex side of the needle 50 at a position nearer the end 52 of the needle than the end 54 of the needle, so that the flap 68 projects from the fold line 70 in a direction roughly diagonally towards tab 60.

With reference to FIG. 5, in which the same reference numerals again refer to the same parts, the flaps 26 and 28 are then folded inwardly over the carrier 58, and downwardly onto the needle 50, respectively about the fold lines 30, 32, to assist in holding the needle in position on the carrier 58.

Finally, to form the package, which is designated 72 in FIG. 6, the panel 16 is folded inwardly over the carrier 58 and flaps 26, 28, about the fold line 22, to hold down the flaps 26, 28, and then a final fold is made at the fold line 24 to bring the panel 18 into abutment with the side of the panel 14 remote from the suture 56, where the flap 46 is inserted through the slot 44 to close the package. The terminal portion 74 of the tab 60, remote from the carrier 58, which projects out of the package, is then folded over at a fold line 76, downwardly onto the outer side of the panel 16, and adhesively secured thereto, to give the package 72 an uninterrupted elongated rectangular outline.

With reference to FIGS. 4, 5 and 6, it will be noted that, in the package 72 of FIG. 6, a portion of the interior of the package is provided, between the panel 12 and the panel 16, in which the needle 50 is located on the carrier 58. The flap 26 closes off one end of this portion of the interior of the package, and the flap 28 partially closes off the other end of this portion of the interior of the package. However, between the end of the fold line 22 adjacent the tab portion 74 and the flap 28, the end of the portion of the interior of the package containing the needle is open, in the region of the cut-out corner 62, to provide a slot along the end edge or shorter edge of the package 72 having one end defined by the end of the fold line 32 remote from the fold line 20, and its other end defined by the end of the fold line 22 adjacent the tab portion 74. It is through this slot that the tab 60 projects outwardly from the interior of the package 72, and it is at this position that the fold line 76 between the terminal portion 74 of the tab 60 and the remainder of the tab 60 is located.

In use, the package 72 will typically be provided, for retail purposes, in a transparent, sealed, plastics/foil sachet or the like sterile outer wrapping (not shown). Shortly before use, the package 72 is removed from this outer wrapping, and the terminal portion 74 of the tab 60 is unstuck from the outside of the panel 16, and folded outwardly so that it extends longitudinally, as shown in FIGS. 4 and 5.

The terminal portion 74 is then pulled in the direction of arrow 78, to remove the needle 50 from the package 72. This pull on the tab 60 urges the carrier 58 in the direction of arrow 78, the flap 68 engaging the convex side of the needle 50, so that the needle is pulled along with the carrier 58.

The trailing end 54 of the needle 50 enters the slot through which the flap 60 projects out of the package, shortly before the convex side of the needle, adjacent said trailing end, engages the flap 28 at the end of said slot, in response to movement of the carrier 58. Engagement between said needle and the flap 28 urges the needle towards the fold line 22. The leading or pointed end 52 of the needle engages said fold line 22, but the trailing end of the needle, which is now outside the package and projecting through said slot, is free to move in a direction towards said fold line 22, i.e. in a direction parallel to the shorter or end edges of the package 72.

Further movement of the carrier 58 in the direction of arrow 78, causes sliding engagement respectively between the leading end 52 of the needle 50 and fold line 22, between the convex side of the needle and the flap 68, and between the convex side of the needle and the flap 28. This sliding engagement· simultaneously causes pivoting in the direction of arrow 80 (see FIG. 4) of the needle relative to the package about the leading end 52 of the needle where it engages the fold line 22, as said leading end 52 slides along said fold line towards the slot from which the needle is emerging. By the time the carrier 58 reaches the flap 28, and can move no further, the needle 50 and tab 60 have reached the positions shown in broken lines in FIG. 5. When it is in this position, the needle can easily and conveniently be grasped by a user, by hand or by means of a suitable surgical instrument, and the needle and suture can be fully withdrawn from said slot, after which the package 72 is discarded.

It will be noted that the end of the slot through which the needle emerges, which is closed off by the flap 28, acts as a cam formation for the needle, which cam formation guides the needle into its position shown in FIG. 6, as the tab 60, 74 is pulled. In this regard the flap 68, where it engages the convex side of the needle, and the fold line 22, where it engages the leading end 52 of the needle, can also be regarded, broadly, as cam formations. In use, they can be regarded as having a camming act on the needle, as it slides over them when the tab 60, 74 is pulled, which camming action co-operates with the camming action of the flap 28, to move and rotate the needle, to present it as shown in FIG. 6.

It is an advantage of the invention that it provides a simple, easily made and conveniently used, inexpensive needle-and-suture package for retailing purposes. Removal of the needle and suture from the package is quick, uncomplicated and easy, and can be performed effectively by a person using surgical gloves. In particular, pulling of the pull tab as shown in FIG. 6 presents the trailing end of the needle in a position where it stands free of the package and tab, in a position where it can safely and easily be gripped by a user and pulled out of the package with the suture attached thereto, either by hand or with a suitable surgical instrument.

Although the invention above has been described with reference to curved needles, its broader aspects can also extend to straight needles, with or without attached sutures. In accordance with these aspects of the invention and with reference to the numerals used in the drawings, a disposable needle package 72 contains a surgical needle 50 and comprises a flattened envelope provided with a needle carrier 58 in its interior on which at least one straight (or curved) needle 50 is supported, the carrier 58 having a pull tab 60 fast therewith and projecting outwardly from a slot in the envelope 72, the carrier 58 being movable in the interior of the envelope 72 towards the slot in response to a pull on the tab 60, into a position in which the needle 50 is at least partially exposed and projects from the interior of the package 72. The needle may have a suture 56 attached thereto and the needle carrier 58 may be held captive in the interior of the envelope. In this arrangement the slot may extend along part of one of the shorter ends of the periphery of the envelope, the needle carrier 58 having a needle-engaging formation 68 fast therewith for urging the needle towards the slot and into engagement with a cam formation fast with the envelope 72, to urge one end of the needle out of the slot and into a position in which it stands free of the envelope 72 and the tab 60.

Instead, the slot may extend along the whole of said shorter edge, the cam being dispensed with. In this case the needle 50 can be attached to the carrier 58 by having its leading end 52 thrust into a thin pad 82 (broken lines in FIG. 4) of a suitable foam material stuck to the surface of the carrier 58 remote from the slot, and its trailing end 54 projecting towards the slot. The pull tab 60 would have its free end 74 stuck to the outside of the package, as shown in FIG. 6, and a pull on the tab to withdraw it from the slot would expose the trailing end of the needle, outside the package and on the carrier or tab. The tab could then be bent or folded downwardly (FIG. 6) away from the trailing end of the needle to present said trailing end for easy grasping. In this construction the blank and package could be simpler than that shown in the drawings, one or more of the flaps 26, 28, 38 or 40 being omitted, or even the whole of panel 12, depending on whether or not the needle has a suture attached thereto.

I claim:

1. A suture envelope containing a curved needle having a blunt end and a pointed end with a suture attached to the blunt end of said needle, said needle having an outer curved surface and an inner curved surface, said envelop being rectangular in shape with a pair of longer side edges and a pair of shorter end edges, a slot extending along at least a portion of one of the shorter end edges, a pull tab extending through said slot, needle carrier means disposed in said envelope and attached to said pull tab, said needle being disposed on said carrier means with the outer curved surface of the needle adjacent one of the longer side edges of the envelope and the blunt end and pointed end of the needle adjacent the other longer side edge of the envelope, and cam means disposed in the envelope and engaging the outer curved surface of the needle whereby upon pulling the pull tab the needle is urged thorough the slot and the needle's orientation relative to the envelope is altered so that an end of the needle is free of the envelope and the pull tab.

2. A suture envelope according to claim 1 wherein the blunt end of the needle is disposed adjacent the slot.

3. A suture envelope according to claim 1 wherein a portion of the shorter end edge of the envelope containing the slot is closed and said closed portion of said shorter end edge is the cam means.

4. A suture envelope according to claim 1 wherein the pull tab extending through the slot is folded onto the outer surface of the envelope and releasably attached thereto.

* * * * *